US00PP24278P3

(12) United States Plant Patent
Menge et al.

(10) Patent No.: US PP24,278 P3
(45) Date of Patent: Mar. 4, 2014

(54) AVOCADO VARIETY NAMED 'UZI'

(50) Latin Name: ***Persea americana* Mill.**
Varietal Denomination: Uzi

(75) Inventors: John A. Menge, Webster, WI (US); Gray E. Martin, Fallbrook, CA (US); Berthold O. Bergh, Riverside, CA (US); Fred B. Guillemet, Chino, CA (US); Lucille Guillemet, legal representative, Chino, CA (US); Brandon S. McKee, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 125 days.

(21) Appl. No.: 13/200,170

(22) Filed: Sep. 19, 2011

(65) Prior Publication Data

US 2013/0074230 P1 Mar. 21, 2013

(51) Int. Cl.
*A01H 5/00* (2006.01)

(52) U.S. Cl.
USPC ..... Plt./200

(58) Field of Classification Search
USPC ..... Plt./200
See application file for complete search history.

*Primary Examiner* — Kent L Bell

(74) *Attorney, Agent, or Firm* — Kilpatrick Townsend & Stockton LLP

(57) ABSTRACT

A new and distinct *Persea americana* variety having strong tolerance to *Phytophthora cinnamomi* when used as a rootstock. It is an extremely vigorous and fast-growing rootstock that is capable of supporting a 'Hass' tree growing to 15 ft. in 2 years. It's yields are generally high and consistent. 'Uzi' leaves exhibit burn due to salt damage, but this does not seem to affect the growth or yield of the 'Hass' variety.

6 Drawing Sheets

Latin name of the genus and species: The avocado cultivar of this invention is botanically identified as *Persea americana* Mill.

Variety denomination: The variety denomination is 'Uzi'.

BACKGROUND OF THE INVENTION

Avocado root rot is the limiting factor for the growth of avocados throughout the world. Avocado root rot is caused by the fungus *Phytophthora cinnamomi*, which attacks and kills the feeder roots of avocado trees. The resultant lack of roots causes the tree to eventually die from water stress. There are a number of varieties of rootstocks that have some tolerance to the disease. These varieties included 'Duke 7' (unpatented), the most commonly planted tolerant rootstock in the world; and 'Thomas' (U.S. Plant Pat. No. 6,628), another root rot tolerant rootstock. However, even with these rootstocks, growers must still use a variety of methods, including mounding, mulching and the applications of chemical fungicides, to keep the tress from dying in many soils. More resistant rootstocks are necessary to eliminate avocado root rot as a major disease threat.

Screening and Greenhouse Evaluation of Rootstocks

'Uzi' was identified and characterized using the following screening protocol. As it is difficult to breed avocados because only one in approximately one thousand flowers actually set fruit, plant breeding blocks of avocados were isolated to prevent out-crossing with susceptible rootstocks. The breeding blocks were made up of various combinations of selected rootstocks including, 'Thomas' (U.S. Plant Pat. No. 6,628), 'Barr Duke' (U.S. Plant Pat. No. 6,627), 'G6', 'Duke 7', 'Duke 9', 'UC 2001', 'UC 2011', 'Toro Canyon' (U.S. Plant Pat. No. 5,642), 'Spencer', 'CR1-71', 'G 810', 'G 875', 'G 755A', 'VC 256', and 'Steyemarkii'. In order to synchronize blooming, attempts were made to girdle late-blooming varieties and spray early-blooming varieties with the pesticide Unicona-zole-P.

Initial screening was carried out by germinating seeds, which were harvested from the breeding blocks, in flats of vermiculite in the greenhouse. *Phytophthora cinnamomi*-infested millet was placed in rows along with the young roots of the test seedlings. After 8-10 weeks roots were evaluated and those with a high percentage of surviving roots were transplanted to soil mix incorporated with *P. cinnamomi*-infested millet. Rootstocks that survived this test were planted and grown in *P. cinnamomi*-infested soils. Survivors were examined more carefully for various types of resistance using asexual propagated material.

a. Root survival—Rootstocks were grown in typical California avocado soils, inoculated with *P. cinnamomi* and evaluated for growth, root length and percent healthy roots.
b. Root regeneration—Rootstocks were grown in soil inoculated with *P. cinnamomi*, treated with Aliette to halt *Phytophthora* root rot and evaluated for root regeneration.
c. Attraction to *P. cinnamomi*—Roots of the rootstocks were placed in water baths with motile zoospores of *P. cinnamomi*. The numbers of spores attracted to the roots were evaluated.

Rootstocks that performed well in the screening and greenhouse evaluations were further tested under field conditions.

Selection of 'Uzi'

'Uzi' was developed at Riverside, Calif. The maternal parent is 'G6' (unpatented) avocado variety. The pollen parent is unknown. Specifically, the 'Uzi' rootstock variety was selected in 1993 from an agricultural operations land located Riverside, Calif. The fruit were collected from the avocado breeding blocks, the seed removed, and planted in vermiculite. The seeds were grown in a greenhouse. The plants were inoculated with the fungus *Phytophthora cinnamomi*. After showing tolerance to the disease, 'Uzi' was chosen as a single plant for further testing. Budwood was collected from the plants and grafted to the stumps of adult avocado trees that had been cut down at Irvine, Calif. The new varieties grew into trees which provided budwood for further testing. At least two 'mother' trees of the variety are growing in Irvine, Calif., along with the germplasm. During screening and evaluation, 'Uzi', which was selected and originally designated 'PP14', distinguished itself from other varieties, including the maternal parent 'G6,' by having a high tolerance against *Phytophthora* root rot. The properties of 'Uzi' were found to be true to type and transmissible by asexual reproduction.

BRIEF SUMMARY OF THE INVENTION

This invention relates to a new and distinct avocado variety. 'Uzi' is an avocado tree having a rootstock that has a high tolerance against *Phytophthora* root rot. It is an extremely vigorous and fast-growing rootstock that is capable of supporting a 'Hass' tree growing to 15 ft. in 2 years. It's yields are generally high and consistent. 'Uzi' leaves exhibit burn due to salt damage, but this does not seem to affect the growth or yield of the 'Hass' variety.

DETAILED DESCRIPTION OF THE INVENTION

Figure 1:
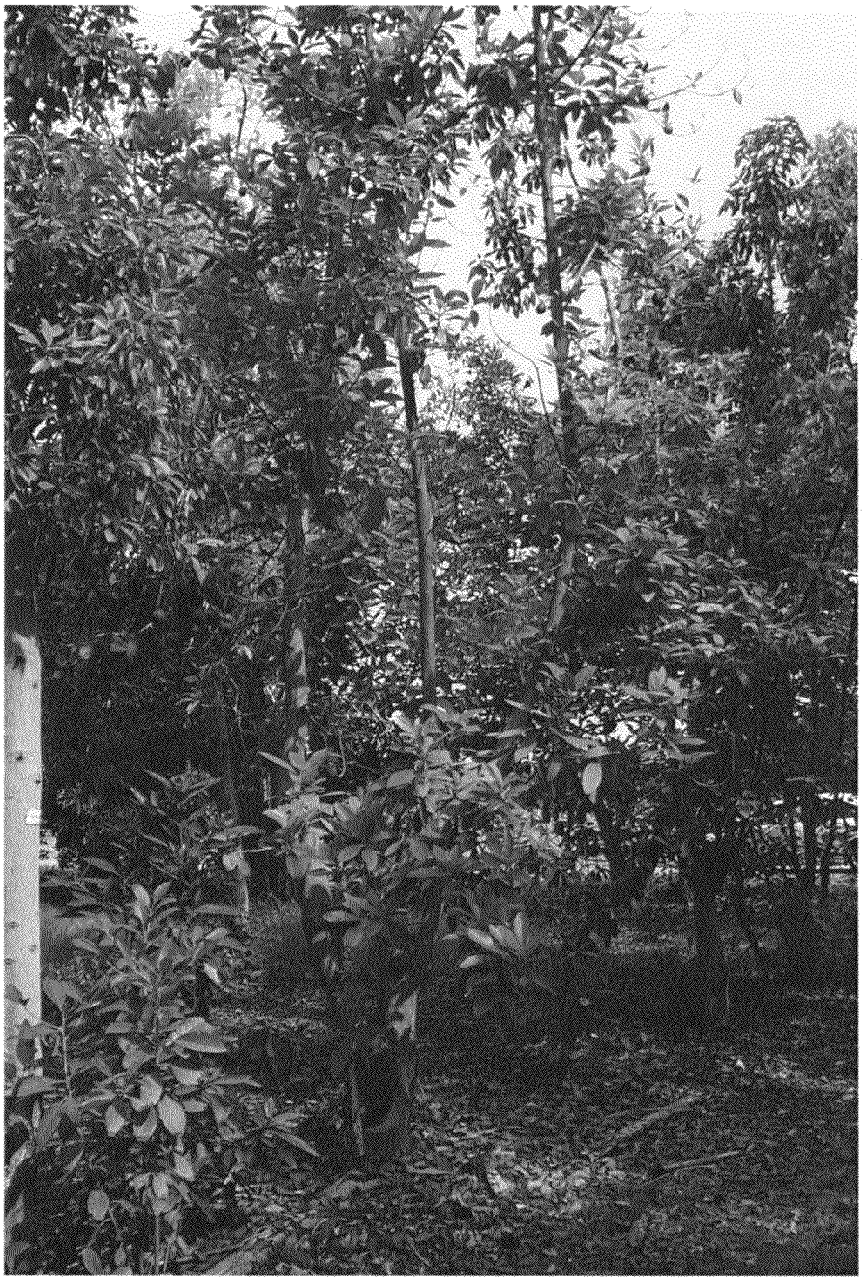
FIG. 1 illustrates a eight-year-old top-worked tree of the 'Uzi' variety while growing in Irvine, Calif.
Figure 2:
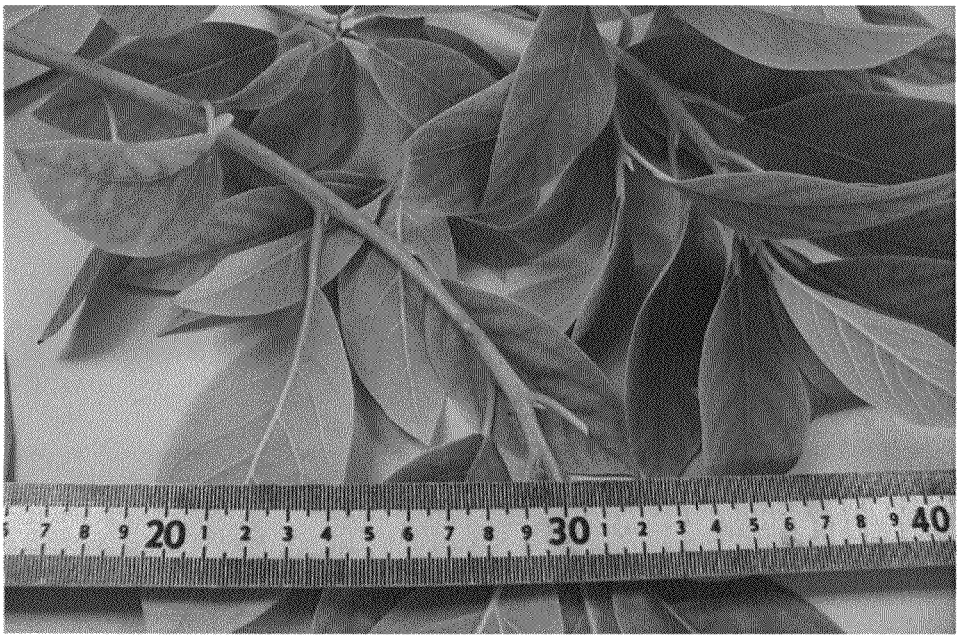
FIG. 2 illustrates typical mature foliage of the 'Uzi' variety with dimensions in centimeters shown at the bottom.
Figure 3:
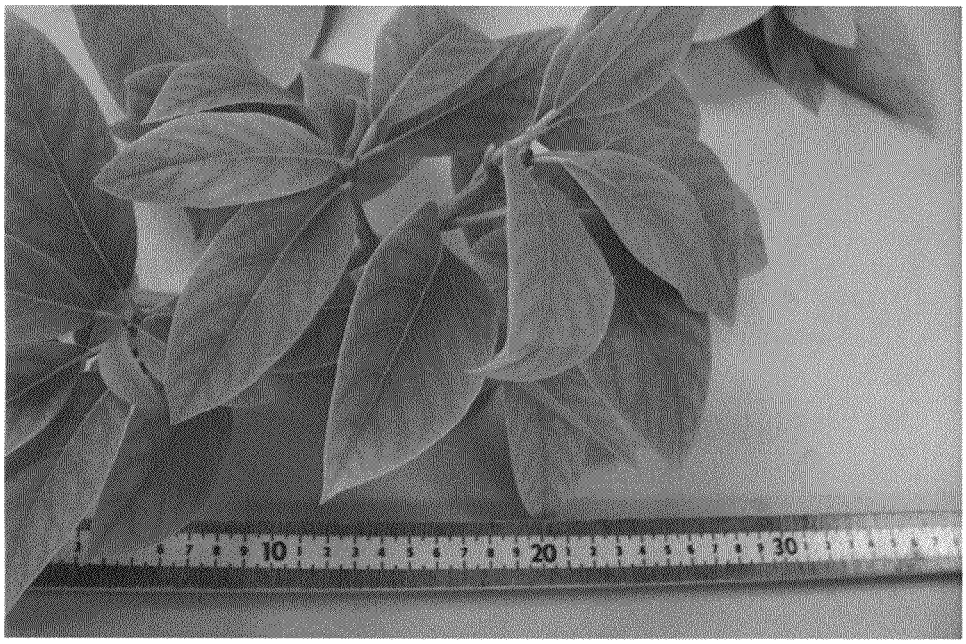
FIG. 3 illustrates typical flush foliage of the 'Uzi' variety with dimensions in centimeters shown at the bottom.
Figure 4A:
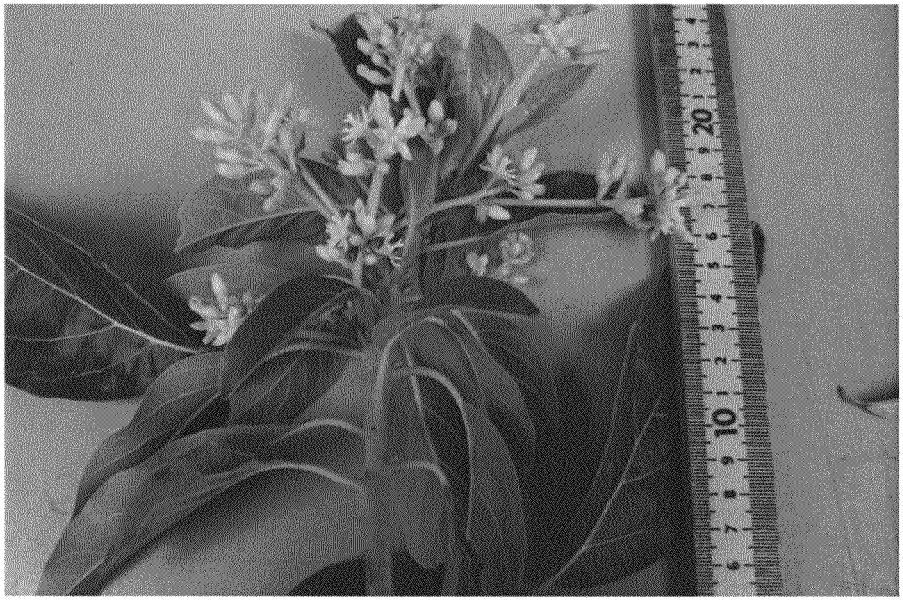
FIG. 4A illustrates typical inflorescence with dimensions in centimeters shown at the right.
Figure 4B:
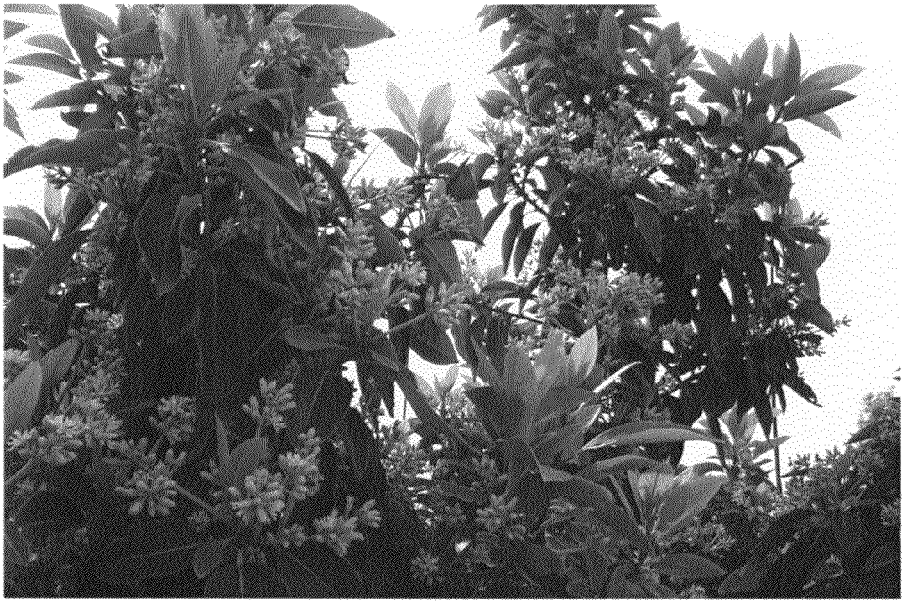
FIG. 4B illustrates typical inflorescence by itself.
Figure 5:
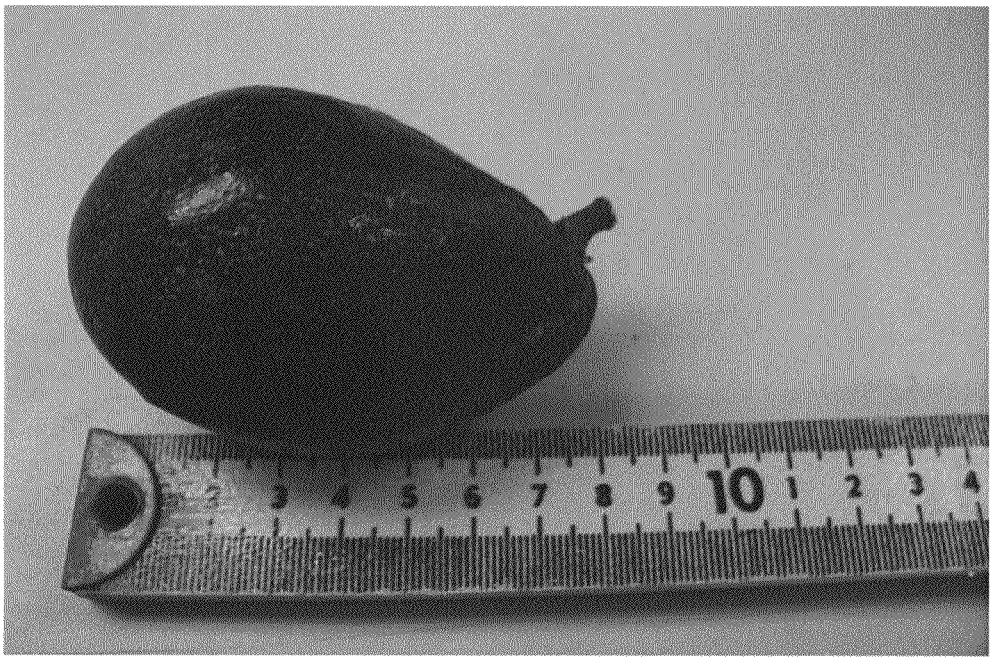
FIG. 5 illustrates a typical external view of the fruit of the 'Uzi' variety, with dimensions in centimeters shown at the bottom.
Figure 6:
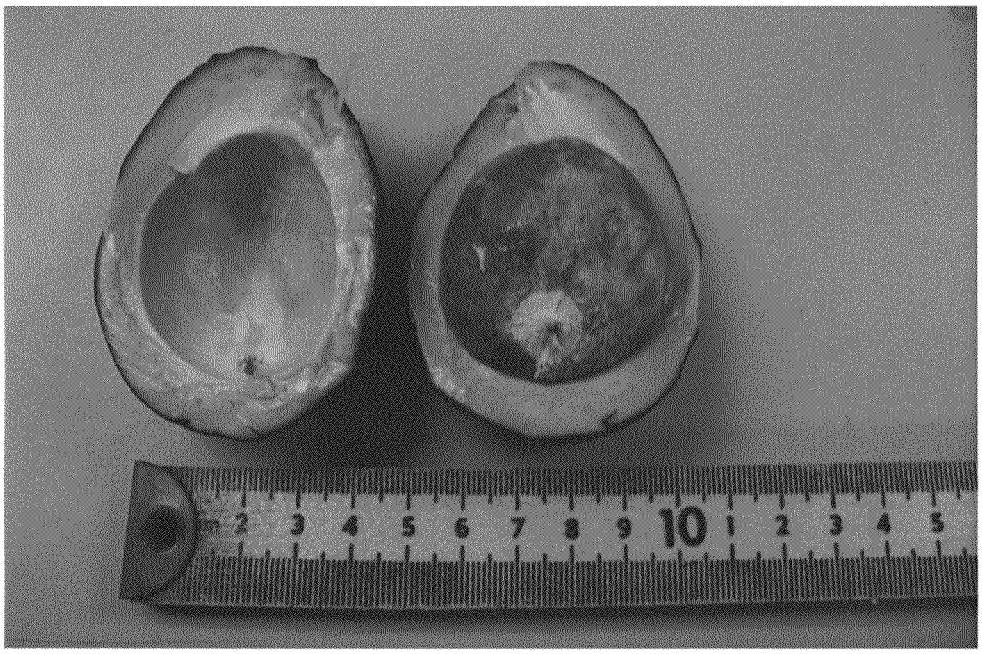
FIG. 6 illustrates typical internal views of the fruit of the 'Uzi' variety, with and without the seed. Dimensions in centimeters are shown at the bottom.

The following is a detailed description of the new 'Uzi' variety, which was taken from an approximately eight-year-old mature tree, with the exception as a rootstock for a specific scion when reference is made to root rot resistance and salinity tolerance. The tree is located in an experimental orchard in Irvine, Calif. and is grafted on a *Persea americana* seedling used as a rootstock.

The Royal Horticultural Society (R.H.S.) color Chart is used herein for the color description of the rind, seed, bark, leaf, flower, flesh color and other interest of the 'Uzi' avocado tree.

Trees, Foliage, and Flowers

Tree:

*Growth habit*.—Vigorous, upright and spreading when compared to the rootstock 'Thomas'.

*Vigor*.—Below are data on the vigor of 'Hass' grafted onto the rootstock 'Uzi', as determined by trunk diameter measurements from trees planted in an orchard with *Phytophthora cinnamomi* in Escondido, Calif.

TABLE 1

| Trunk diameter (cm) | | | | | |
|---|---|---|---|---|---|
| Rootstock | year 1 | year 2 | year 3 | year 4 | year 5 |
| PP # 14 'Uzi' | 2.85 | 5.14 | 8.57 | 10.6 | 12.54 |
| Thomas | 2.44 | 4.29 | 6.75 | 8.40 | 10.84 |

Escondido Ca., with Hass scion

TABLE 2

| Canopy volume (cubic feet) | | | | | |
|---|---|---|---|---|---|
| Rootstock | year 1 | year 2 | year 3 | year 4 | year 5 |
| PP # 14 'Uzi'. | 21.86 | 163.21 | 504.3 | 669 | 1338.2 |
| Thomas | 13.56 | 84.48 | 388.5 | 367. | 1076.2 |

Escondido Ca., with Hass scion

*Size*.—Large. The typical canopy size of a three year old top-worked 'Thomas' is 388 cu.ft. By comparison the canopy size of a three year old topworked 'Uzi' is 504 cu.ft. The tree is 610-915 cm in height when fully grown at the orchard site in Irvine, Calif.

Branch:

*Color*.—The color of the one year old branch is green (RHS 146C).

*Smoothness*.—The bark of a one year old branch is smooth.

*Lenticels*.—The lenticels of a one year old branch are conspicuous.

Main stem:

*Color*.—Brown (RHS N 200C and N 200D).

*Texture of bark*.—Corky.

Young shoot (flush):

*Intensity of anthocyanin coloration*.—Weak.

*Anthocyanin coloration*.—Grayed-orange (RHS 165B).

*Color*.—Grayed-orange (RHS 165B).

*Conspicuousness of lenticels*.—Medium.

*Color of lenticels*.—Grayed-purple (RHS 185A).

*Size of lenticels*.—1.0-3.0 mm long.

*Concentration of lenticels*.—+/−25 lenticels per square cm.

*Color of upper side*.—Grayed-green (RHS 194B).

*Glossiness of upper side*.—Medium.

*Color of lower surface*.—Grayed-green (RHS 193B).

Mature leaf:

*Length*.—13.0 cm.

*Width*.—5.5 cm.

*Ratio length/width*.—2.4.

*Shape*.—Elliptical.

*Color of upper side*.—Green (RHS 139A).

*Color of lower side*.—Green (RHS 137B).

*Glossiness of upper side*.—Medium-high.

*Prominence of veins on lower side*.—Prominent and in relief.

*Color of veins*.—Yellow-green (RHS 145A).

*General shape and cross-section*.—Flat, slightly concave.

*Reflexing of apex*.—Absent.

*Color of petiole*.—Yellow-green (RHS 144A).

*Anise aroma*.—Present.

*Margin*.—Undulation of margin is weak, and the leaf margin is entire.
*Leaf apex shape*.—Acute.
*Leaf base shape*.—Elliptical.
*Length of leaf petiole*.—Approximately 2.8 cm.
*Diameter of leaf petiole*.—Approximately 2.0 mm.
*Leaf arrangement*.—upright.

Flower:

*Bud size*.—Approximately 3 mm in length and approximately 2.5 mm in diameter.
*Bud shape*.—Ovoid.
*Bud color*.—Grayed-green (RHS 197C).
*Opening*.—Belongs to group "B", female opening (i.e. with mature pistil) occurs in the afternoon, the flower closes over night, and the male opening (i.e. with mature stamens) occurs the next morning; the flower's opening cycle lasts 20-24 hours.
*Petals*.—Borne in two whorls of three perianth lobes. The petals possess entire margins and petal coloration is near yellow-green (RHS 151D). Both the upper and lower petal surfaces are near yellow-green (RHS 151D).
*Stamen*.—There are commonly nine fertile stamens with each having two basal nectar glands that are grayed-orange (RHS 174A) in color and three staminodla. The anthers are tetrathecal.
*Pistil*.—The single pistil with a slender style and small stigmatic surface has one carpel with one ovule. The ovary is superior.
*Sepals*.—There are 6 sepals which are approximately 5 mm in length and approximately 3 mm in width, and the color of both sepal surfaces is yellow-green (RHS 151A).
*Pedicel*.—Commonly approximately 6 mm in length and approximately 2.0 mm in diameter. The coloration is near yellow-green (RHS 151B).
*Peduncles*.—Approximately 5.7 cm in length and approximately 3.0 mm in diameter. The coloration is yellow-green (RHS 151A).
*Number of flowers on inflorescence*.—Approximately 108-135 flowers per inflorescence.
*Fragrance*.—Absent.
*Bloom*.—Bloom period at Riverside, Calif. experiment station varies with cultural conditions. On average 'Uzi' has been found to bloom from 25$^{th}$ of January through the 15$^{th}$ of March.

Fruit, Fruit and Production Characteristics

Fruit:

*Length*.13 7.0 cm.
*Width*.—5.5 cm.
*Ratio length/width*.—1.3.
*Weight*.—53.4 grams.
*Shape*.—Narrowly obovate, with an apex diameter of approximately 2.2 cm and a base diameter of approximately 3.9 cm at the widest point.
*Color of skin* (*when ripe*).—Grayed-purple (RHS N186).
*Texture of skin*.—Smooth.
*Presence of longitudinal ridges*.—Absent.
*Thickness of skin*.—Thin.
*Adherence of skin to flesh*.—Weak.
*Main color of flesh*.—Yellow-green (RHS 144B).
*Color of intensely colored area of flesh next to skin*.—Yellow-green (RHS 144A).
*Width of intensely colored area next to skin*.—1.0 mm.
*Conspicuousness of fibers in flesh*.—Conspicuous.

Seed:

*Length*.—4.7 cm.
*Width*.—4.0 cm.
*Weight*.—11.9 grams.
*Shape* (*in longitudinal section*).—Circular.
*Shape* (*in cross section*).—Circular.
*Color of seed coat* (*fresh*).—Grayed-orange (RHS 177A).
*Cotyledon color*.—Orange-white (RHS 159B).
*Time of harvesting*.—'Uzi' fruit ripen in September/October (in Riverside Calif.).
*Resistance to pests*.—Strong resistance to *Phytophthora cinnamomi*.
*Tolerance to salinity*.—Medium.
*Market use*.—The fruit of 'Uzi' are not intended for market use, but rather the variety is used as a rootstock onto which commercial varieties, such as 'Hass' are grafted.

TABLE 3

Rootstock rating at Santana, Ventura County, August 2001[1]

| Rootstock | Tree rating (0-5; 5 = dead) | Canopy volume (cu ft) | Trunk diameter (cm) | No. trees dead |
|---|---|---|---|---|
| 'Steddom' | 0.80 a | 13.89 a | 1.92 a | 1 |
| 'Merensky II' | 0.90 a | 15.10 a | 1.48 a | 1 |
| 'Uzi' | 0.90 a | 16.92 a | 2.02 a | 0 |
| 'Zentmyer' | 1.05 a | 16.48 a | 2.05 a | 1 |
| 'G755A (Brokaw)' | 1.65 a | 5.55 a | 1.62 a | 1 |
| 'Medina' | 1.90 a | 12.66 a | 1.70 a | 2 |
| 'Berg' | 2.20 a | 13.80 a | 1.29 a | 4 |
| 'McKee' | 2.35 a | 9.05 a | 1.52 a | 1 |
| 'Duke 7' | 2.50 a | 11.40 a | 1.24 a | 4 |
| 'Thomas' | 2.65 a | 10.22 a | 1.15 a | 4 |
| 'G755 A (C&M)' | 2.75 a | 11.66 a | 1.49 a | 2 |
| 'UC 2023' | 3.00 a | 6.21 a | 1.25 a | 3 |

[1]Mean values in each column followed by identical letters are not statistically different according to Waller's k-ratio t test.

TABLE 4

Rootstock rating at Santana, Ventura County, November 2002. Two-year trial to-date.

| 'Rootstock' | Tree rating (0-5; 5 = dead) | Canopy volume (cu ft) | Trunk diameter (cm) | Fruit rating (0-5; 5 = heavy) |
|---|---|---|---|---|
| 'Merensky II' | 0.17 d | 72.27 abc | 3.49 ab | 0.78 bcd |
| 'Uzi' | 0.50 cd | 69.64 abcd | 3.64 a | 2.50 a |
| 'Steddom' | 1.00 bcd | 67.95 abcd | 2.94 abc | 1.70 abc |
| 'Medina' | 1.06 bcd | 79.89 ab | 3.26 ab | 0.00 d |
| 'Zentmyer' | 1.50 bcd | 81.44 a | 3.19 ab | 0.60 bcd |
| 'Duke 7' | 1.67 bcd | 32.48 abcde | 2.31 abcd | 1.11 abcd |
| 'Berg' | 1.72 bcd | 46.57 abcde | 2.21 abcd | 2.00 ab |
| 'McKee' | 1.78 abcd | 30.92 bcde | 2.24 abcd | 0.22 cd |
| 'G755A (Brokaw)' | 2.30 abcd | 19.98 de | 1.90 bcd | 0.10 d |
| 'Thomas' | 2.60 abc | 31.50 bcde | 2.02 abcd | 0.30 cd |
| 'UC 2023' | 2.95 ab | 25.50 cde | 1.41 cd | 0.20 d |
| 'G755A (C&M)' | 4.00 a | 15.71 e | 0.82 d | 0.00 d. |

TABLE 4-continued

Rootstock rating at Santana, Ventura County, November 2002.
Two-year trial to-date.

| Rootstock | Tip burn rating (0-5) | Canker rating (0-5) | No. trees dead |
|---|---|---|---|
| 'Merensky II' | 0.00 a | 0.33 a | 0/9 |
| 'Uzi' | 0.33 a | 0.00 a | 1/10 |
| 'Steddom' | 0.25 a | 0.00 a | 2/10 |
| 'Medina' | 0.75 a | 0.00 a | 1/9 |
| 'Zentmyer' | 0.38 a | 0.63 a | 1/10 |
| 'Duke 7' | 0.38 a | 0.38 a | 3/9 |
| 'Berg' | 0.17 a | 0.83 a | 3/9 |
| 'McKee' | 0.43 a | 0.29 a | 2/10 |
| 'G755A (Brokaw)' | 0.29 a | 0.14 a | 3/10 |
| 'Thomas' | 0.17 a | 1.00 a | 4/10 |
| 'UC 2023' | 0.00 a | 0.00 a | 5/10 |
| 'G755A (C&M)' | — | — | 8/10 |

TABLE 5

Rootstock ratings of avocado trees planted in root rot soil at Escondido, July 2002

| Rootstocks | Tree rating 0-5; 5 = dead | Canopy volume Cu ft | Trunk diameter Cm | Fruit set rating 0-5; 5 = heavy |
|---|---|---|---|---|
| 'Zentmyer' | 0.00 c | 397.4 abc | 7.12 bcd | 1.53 cd |
| 'Rio Frio' | 0.00 c | 313.5 cdef | 6.33 cdef | 2.13 bcd |
| 'Merens I' | 0.00 c | 543.6 a | 8.74 a | 3.50 a |
| 'Merensk II' | 0.02 c | 409.0 abc | 7.81 abc | 2.84 ab |
| 'VC 241' | 0.06 c | 238.4 defg | 6.19 defg | 1.41 cd |
| 'Uzi' | 0.29 bc | 504.3 ab | 8.57 ab | 2.76 ab |
| 'Steddom' | 0.36 bc | 376.1 bcde | 7.07 bcd | 2.43 bc |
| 'Thomas' | 0.44 bc | 388.5 bcd | 6.75 cde | 1.12 de |
| 'Guillemet' | 0.59 bc | 192.0 fgh | 4.90 fgh | 1.12 de |
| 'Spencer sdlg' | 0.63 bc | 225.8 efg | 5.24 efgh | 1.56 cd |
| 'Leo' | 0.67 bc | 288.2 cdef | 5.89 defgh | 1.60 cd |
| 'Spencer clonal' | 0.69 bc | 163.8 fgh | 4.65 gh | 1.54 cd |
| 'Duke 7' | 1.00 b | 129.3 gh | 4.38 h | 1.47 cd |
| 'G755A' | 0.16 b | 294.1 cdef | 5.86 defgh | 1.56 cd |
| 'PolyN' | 4.12 a | 65.6 h | 1.26 i | 0.24 e |

| Rootstocks | Tip Burn | Cankers | Dead |
|---|---|---|---|
| | Number trees affected | | |
| 'Zentmyer' | 0 | 0 | 0/15 |
| 'Rio Frio' | 0 | 0 | 0/16 |
| 'Merens I' | 0 | 0 | 0/14 |
| 'Merensk II' | 0 | 1 | 0/17 |
| 'VC 241' | 0 | 0 | 0/16 |
| 'Uzi' | 2 | 0 | 1/17 |
| 'Steddom' | 0 | 0 | 1/14 |
| 'Thomas' | 0 | 0 | 1/17 |
| 'Guillemet' | 3 | 1 | 2/17 |
| 'Spencer sdlg' | 0 | 0 | 2/16 |
| 'Leo' | 0 | 0 | 2/15 |
| 'Spencer clonal' | 0 | 0 | 5/16 |
| 'Duke 7' | 0 | 0 | 3/15 |
| 'G755A' | 2 | 1 | 3/16 |
| 'PolyN' | 0 | 0 | 14/17 |

TABLE 6 rootstock trial tree ratio April 2003[1].
Four-year trial to-date

| Rootstock | Tree rating (0-5; 5 = dead) | Canopy volume (cu ft) | Trunk diam. (cm) | Salt |
|---|---|---|---|---|
| 'MerenI' | 0.00d | 551ab | 10.7a | 0.08cd |
| 'VC241' | 0.06d | 281efgh | 8.0abc | 0.03cd |
| 'Rio Frio' | 0.07d | 362efcd | 8.7abc | 0.00d |
| 'Zentmyer' | 0.07d | 410bcde | 9.2ab | 0.32bc |
| 'MerenII' | 0.18d | 532abc | 9.4ab | 0.21dc |
| 'Spen sdlg' | 0.36d | 263efgh | 6.9bc | 0.00d |
| 'Uzi' | 0.38d | 669a | 10.6a | 0.68a |
| 'Steddom' | 0.39d | 478bcd | 8.6abc | 0.32bc |
| 'Thomas' | 0.47cd | 367cdef | 8.4abc | 0.62ab |
| 'Leo' | 0.77cbd | 274efgh | 7.3abc | 0.13cd |
| 'Guillemet' | 0.83cbd | 190ghi | 6.2bc | 0.13cd |
| 'Duke7' | 1.34cb | 127hi | 8.8abc | 0.16cd |
| 'Spen cl' | 1.44b | 211fghi | 5.3c | 0.12cd |
| 'G755A' | 1.69b | 322defg | 7.0bc | 0.25cd |
| 'PolyN' | 4.15a | 77i | 1.5d | 0.06cd |

| Rootstock | Canker (0-5; 5 = heavy) | Fruit rating[2] | Dead trees (%) |
|---|---|---|---|
| 'MerenI' | 0a | 2.97abc | 0 |
| 'VC241' | 0a | 3.41ab | 0 |
| 'Rio Frio' | 0a | 3.73a | 0 |
| 'Zentmyer' | 0a | 3.71a | 0 |
| 'MerenII' | 0.1a | 2.97abc | 0 |
| 'Spen sdlg' | 0a | 3.57ab | 7 |
| 'Uzi' | 0a | 3.47ab | 6 |
| 'Steddom' | 0a | 3.75a | 7 |
| 'Thomas' | 0a | 3.53ab | 6 |
| 'Leo' | 0a | 3.29ab | 13 |
| 'Guillemet' | 0a | 2.90abc | 13 |
| 'Duke7' | 0a | 1.53de | 19 |
| 'Spen cl' | 0a | 2.35bcd | 23 |
| 'G755A' | 0a | 1.78cd | 25 |
| 'PolyN' | 0a | 0.29e | 82 |

[1]Mean values in each column followed by identical letters are not statistically different according to Waller's k-ratio t test.
[2]Fruit was rated in November 2003.

TABLE 7

Temecula, yield 2003[1;2].
Four year trial to-date.

| Rootstock | Fruit weight/ tree (kg) | Number fruit/tree | Fruit weight (kg) |
|---|---|---|---|
| 'Zentmyer' | 15.89a | 68.64a | 0.219a |
| 'Uzi' | 13.99ab | 59.24ab | 0.195ab |
| 'Spencer seedling' | 12.52ab | 56.27ab | 0.181ab |
| 'Merensky II' | 11.83ab | 51.12ab | 0.185ab |
| 'Rio Frio' | 10.87abc | 51.33ab | 0.187ab |
| 'Steddom' | 10.01abc | 46.20abc | 0.175abc |
| 'Thomas' | 8.50abcd | 40.12abcd | 0.154abc |
| 'G755A' | 8.08abcd | 34.56abcd | 0.116bc |
| 'VC241' | 7.44bcd | 31.75bcd | 0.202ab |
| 'Guillemet' | 7.42bcd | 30.00bcd | 0.196ab |
| 'Spencer clonal' | 6.99bcd | 32.00bcd | 0.136abc |
| 'Merensky I' | 6.95bcd | 32.08bcd | 0.148abc |
| 'Leo' | 6.53bcd | 28.14bcd | 0.140abc |
| 'Duke 7' | 3.33cd | 14.81cd | 0.138abc |
| 'PolyN' | 1.72d | 5.71d | 0.076c |

[1]Mean values in each column followed by identical letters are not statistically different according to Waller's k-ratio t test.
[2]Only fruit which were grade size were picked; remaining fruit on trees to be picked later.

TABLE 8

Escondido, Tree ratings, July 2002

| Rootstock | Tree rating (0-5; 5 = dead) | Canopy vol. (cu ft) | Trunk diam (cm) | No. trees Dead | No. trees w/tip burn | No. trees w/canker |
|---|---|---|---|---|---|---|
| 'Uzi' | 0.039 b | 34.69 a | 2.43 a | 0 | 6 | 0 |
| 'Guillemet' | 0.042 b | 22.86 a | 2.06 a | 0 | 4 | 0 |
| 'Zentmyer' | 0.077 b | 22.40 a | 2.25 a | 0 | 2 | 0 |
| 'Spencer sdlg' | 0.536 b | 27.81 a | 2.01 a | 0 | 2 | 1 |
| 'Steddom' | 0.615 b | 18.93 a | 1.99 a | 1 | 0 | 0 |
| 'Berg' | 0.714 b | 21.42 a | 1.98 a | 0 | 1 | 2 |
| 'Merensky II' | 0.750 b | 32.07 a | 2.10 a | 2 | 0 | 1 |
| 'Elinor' | 0.786 b | 29.44 a | 2.03 a | 1 | 0 | 2 |
| 'Thomas' | 0.846 b | 23.07 a | 1.85 a | 1 | 2 | 0 |
| 'Pond' | 1.00 ab | 30.55 a | 2.15 a | 1 | 0 | 2 |
| 'Crowley' | 1.083 ab | 23.78 a | 1.86 a | 2 | 1 | 0 |
| 'G755A' | 1.231 ab | 22.64 a | 1.85 a | 2 | 0 | 0 |
| 'Duke 9' | 2.270 a | 9.40 a | 1.07 b | 5 | 0 | 0 |

There were significant differences at P = 0.01 between blocks for all tree parameters analyzed.

TABLE 9 tree ratings, April 2003. Two-year trial to-date.

| Rootstock | Tree rating (0-5; 5 = dead) | Canopy vol (cu ft) | Trunk diam (cm) | Fruit rating (0-5; 5 = heavy) |
|---|---|---|---|---|
| 'Uzi' | 0.267 c | 88.76 a | 4.193 a | 0.0 a |
| 'Berg' | 0.531 c | 44.16 a | 2.956 bc | 0.0 a |
| 'Zentmyer' | 0.600 c | 54.37 a | 3.393 ab | 0.0 a |
| 'Merensky II' | 0.833 bc | 68.49 a | 3.333 ab | 0.0 a |
| 'Steddom' | 0.867 bc | 56.42 a | 3.127 ab | 0.0 a |
| 'Pond' | 0.906 bc | 55.05 a | 3.188 ab | 0.0 a |
| 'Spenser sdlg' | 0.906 bc | 51.45 a | 2.988 bc | 0.0 a |
| 'Crowley' | 0.964 bc | 42.05 a | 3.021 bc | 0.0 a |
| 'Thomas' | 1.071 bc | 49.99 a | 2.900 bc | 0.0 a |
| 'Guillemet' | 0.167 abc | 43.64 a | 2.960 bc | 0.1 a |
| 'Elinor' | 1.393 abc | 58.40 a | 2.864 bc | 0.0 a |
| 'G755A' | 2.156 ab | 44.21 a | 2.819 bc | 0.0 a |
| 'Duke 9' | 2.577 a | 32.16 a | 1.885 c | 0.0 a |

| Rootstock | Salt rating (0-5; 5 = severe) | Canker rating (0-5; 5 = severe) | No. trees Dead (%) |
|---|---|---|---|
| 'Uzi' | 0.933 ab | 0.000 a | 0 |
| 'Berg' | 0.633 abcd | 0.000 a | 6 |
| 'Zentmyer' | 1.000 a | 0.000 a | 7 |
| 'Merensky II' | 0.154 cd | 0.308 a | 13 |
| 'Steddom' | 0.321 bcd | 0.286 a | 7 |
| 'Pond' | 0.767 abc | 0.200 a | 6 |
| 'Spenser sdlg' | 0.300 bcd | 0.200 a | 6 |
| 'Crowley' | 0.083 d | 0.000 a | 14 |
| 'Thomas' | 0.731 abc | 0.000 a | 0 |
| 'Guillemet' | 0.615 abcd | 0.133 a | 13 |
| 'Elinor' | 0.333 bcd | 0.167 a | 14 |
| 'G755A' | 0.846 ab | 0.077 a | 13 |
| 'Duke 9' | 0.313 bcd | 0.500 a | 38 |

TABLE 10

Temecula rootstock ratings, Sept 2002

| Rootstock | Tree rating (0-5; 5 = dead) | Canopy vol. (cu ft) | Trunk diam (cm) | Fruit rating (0-5; 5 = heavy) |
|---|---|---|---|---|
| 'Zentmyer' | 0.400 c | 40.70 ab | 2.79 a | 0.00 b |
| 'Crowley' | 0.618 c | 40.38 ab | 2.86 a | 0.00 b |
| 'Elinor' | 0.824 c | 40.52 ab | 2.54 a | 0.00 b |
| 'Guillemet' | 0.882 bc | 39.13 ab | 2.42 a | 0.00 b |
| 'Steddom' | 0.969 bc | 29.20 bc | 2.13 ab | 1.16 a |
| 'Thomas' | 0.969 bc | 31.46 bc | 2.13 ab | 0.00 b |
| 'Pond' | 1.088 bc | 54.08 a | 2.78 a | 0.00 b |
| 'Uzi' | 1.188 bc | 35.08 ab | 2.56 a | 0.00 b |
| 'G755A' | 2.088 ab | 37.85 ab | 2.41 a | 0.00 b |
| 'Spencer sdlg' | 2.906 a | 11.96 c | 1.39 b | 0.00 b |

| Rootstock | Salt damage (0-5; 5 = heavy) | Cankers (0-5; 5 = heavy) | No. trees dead |
|---|---|---|---|
| 'Zentmyer' | 1.50 ab | 0.00 a | 0/15 |
| 'Crowley' | 1.34 b | 0.00 a | 1/17 |
| 'Elinor' | 1.59 ab | 0.00 a | 1/17 |
| 'Guillemet' | 1.41 b | 0.00 a | 2/17 |
| 'Steddom' | 1.54 ab | 0.50 a | 2/16 |
| 'Thomas' | 1.50 ab | 0.00 a | 3/16 |
| 'Pond' | 1.40 b | 0.00 a | 2/17 |
| 'Uzi' | 1.64 ab | 0.00 a | 2/16 |
| 'G755A' | 2.50 ab | 0.36 a | 4/17 |
| 'Spencer sdlg' | 2.63 a | 0.00 a | 4/16 |

TABLE 11

Temecula, rootstock ratings, December 2003.
Two-year trial to-date

| Rootstock | Tree rating (0-5; 5 = dead) | Canopy vol (cu ft) | Trunk diam (cm) | Fruit rating (0-5; 5 = heavy) |
|---|---|---|---|---|
| 'Zentmyer' | 0.313c | 207.27a | 6.23a | 2.063a |
| 'Pond' | 0.906c | 307.04a | 5.75a | 1.813a |
| 'Elinor' | 0.912c | 170.37a | 4.80a. | 1.059a |
| 'Guillemet' | 1.059c | 199.37a | 5.73a | 0.882a |
| 'Uzi' | 1.094bc | 206.04a | 4.35a | 0.813a |
| 'Crowley' | 1.250bc | 144.14a | 5.04a | 1.438a |
| 'Steddom' | 1.281bc | 254.94a | 4.89a | 1.188a |
| 'Thomas' | 1.313be | 226.39a | 5.16a | 1.375a |
| 'G755A' | 2.438ab | 175.55a | 5.23a | 0.625a |
| 'Spencer sdlg' | 2.813a | 42.12a | 2.26a | 0.519a |

| Rootstock | Salt damage (0-5; 5 = heavy) | Cankers (0-5; 5 = heavy) | Trees dead (%) |
|---|---|---|---|
| 'Zentmyer' | 1.188ab | 0.000a | 0 |
| 'Pond' | 0.321cd | 0.000a | 13 |
| 'Elinor' | 0.469cd | 0.000a | 6 |
| 'Guillemet' | 0.893abc | 0.000a | 18 |
| 'Uzi' | 0.769abcd | 0.000a | 19 |
| 'Crowley' | 0.731abcd | 0.000a | 19 |
| 'Steddom' | 0.167d | 0.000a | 25 |
| 'Thomas' | 1.308a | 0.000a | 19 |
| 'G755A' | 1.167ab | 0.000a | 25 |
| 'Spencer sdlg' | 0.500bcd | 0.000a | 44 |

What is claimed is:

1. A new and distinct rootstock variety of avocado tree having the characteristics substantially as described and illustrated herein.

* * * * *